(12) United States Patent
Lerm et al.

(10) Patent No.: US 8,022,231 B2
(45) Date of Patent: Sep. 20, 2011

(54) PROCESS FOR PREPARING MONOCHLOROETHYLENE CARBONATE AND SUBSEQUENT CONVERSION TO VINYLENE CARBONATE

(75) Inventors: Marco Lerm, Erkelenz (DE); Joerg Lotz, Kalbach (DE); Klaus Stadtmueller, Alzenau (DE)

(73) Assignee: Evonik Degussa GmbH, Essen (DE)

( * ) Notice: Subject to any disclaimer, the term of this patent is extended or adjusted under 35 U.S.C. 154(b) by 354 days.

(21) Appl. No.: 12/236,765

(22) Filed: Sep. 24, 2008

(65) Prior Publication Data

US 2009/0082586 A1    Mar. 26, 2009

(30) Foreign Application Priority Data

Sep. 24, 2007  (EP) .................................. 07117053

(51) Int. Cl.
*C07D 317/08* (2006.01)
(52) U.S. Cl. ...................................................... 549/229
(58) Field of Classification Search .................... 549/229
See application file for complete search history.

(56) References Cited

U.S. PATENT DOCUMENTS 6,395,908 B1 *  5/2002  Seifert et al. .................. 549/229

FOREIGN PATENT DOCUMENTS

| CN | 1733756 A | 2/2006 |
| EP | 1 101 762 A1 | 5/2001 |
| JP | 2007-91604 | 4/2007 |

OTHER PUBLICATIONS

Chen et al., 2006, CAS: 145:27974.*
Richard G. Finke, et al., "Model Studies of Coenzyme $B_{12}$ Dependent Diol Dehydratase. Synthetic, Physical Property, and Product Studies of Two Key, Cobalt-Bound, Putative Diol Dehydratase Intermediates", Journal of the American Chemical Society, vol. 105, No. 26, XP002277223, Jan. 1, 1983, pp. 7592-7604.
Newman, et al., "Vinylene Carbonate", Journal of the American Chemical Society, vol. 75, No. 5, XP002507107, Mar. 5, 1953, pp. 1263-1264.
Newman, et al., "Synthesis and Reactions of Vinylene Carbonate", Journal of the American Chemical Society, vol. 77, No. 14, XP002507108, Jul. 20, 1955, pp. 3789-3793.

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

Processes for preparing monochloroethylene carbonate include reacting ethylene carbonate with chlorine gas in a liquid phase under irradiation of UV light and introducing a separate feed of an inert gas into the liquid phase. Monochloroethylene carbonate may be subsequently converted to vinylene carbonate.

18 Claims, 1 Drawing Sheet

PROCESS FOR PREPARING MONOCHLOROETHYLENE CARBONATE AND SUBSEQUENT CONVERSION TO VINYLENE CARBONATE

CROSS REFERENCE TO RELATED APPLICATIONS

This application claims priority to European Patent Application Number 07117053.4, filed Sep. 24, 2007, the disclosure of which is incorporated herein by reference in its entirety.

BACKGROUND

Embodiments of the present invention relate to a process for preparing monochloroethylene carbonate from ethylene carbonate, as well as to a process comprising the further conversion of the monochloroethylene carbonate to vinylene carbonate.

Vinylene carbonate is an important intermediate for the synthesis of pharmaceuticals, plant protection agents, polymers, especially for lacquers, and various other chemicals. One important use of vinylene carbonate is as an additive to solutions for batteries, especially for lithium ion batteries. Lithium ion batteries are, for example, used as storage batteries in hybrid electric vehicles.

Generally, vinylene carbonate is prepared from monochloroethylene carbonate by eliminating hydrogen chloride by means of a tertiary amine, usually triethylamine, in an organic solvent. The monochloroethylene carbonate used as a starting material in this elimination reaction is prepared by radical chlorination of ethylene carbonate. Examples of chlorination agents include sulfuryl chloride in combination with a radical initiator, or chlorine gas under the irradiation of UV light. Hydrogen chloride inevitably evolving as a by-product favors the formation of unwanted chlorinated decomposition products of ethylene carbonate. These unwanted chlorinated decomposition products present in the monochloroethylene carbonate which is—for economical reasons—usually directly employed in the synthesis of vinylene carbonate without any purification result in impurities of the final vinylene carbonate product which are difficult to remove. Consequently, a time-consuming and thus expensive recrystallization step is necessary in addition to several distillation steps in order to obtain vinylene carbonate having a high purity, e.g., required for battery applications.

JP-A-2007091604 describes a method for producing monochloroethylene carbonate comprising reacting ethylene carbonate with chlorine gas under the irradiation of light, wherein the chlorine gas is mixed with an inert gas and the gas mixture is then introduced into the reaction system. The method is said to improve the purity of the monochloroethylene carbonate product. However, the purity may still be insufficient for some uses.

SUMMARY

It is an object of the present invention to provide new processes for the preparation of monochloroethylene carbonate resulting in the formation of less unwanted chlorinated decomposition products.

The object is met by processes for preparing monochloroethylene carbonate comprising: (a) reacting ethylene carbonate with chlorine gas in the liquid phase under the irradiation of UV light and (b) introducing a separate feed of an inert gas into the liquid phase.

Embodiments of the invention are further directed to processes for preparing vinylene carbonate comprising preparing monochloroethylene carbonate as described above and (ii) subjecting the obtained product(s) to an elimination reaction wherein hydrogen chloride is abstracted from monochloroethylene carbonate to form vinylene carbonate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF EXEMPLARY EMBODIMENTS

Figure 1:
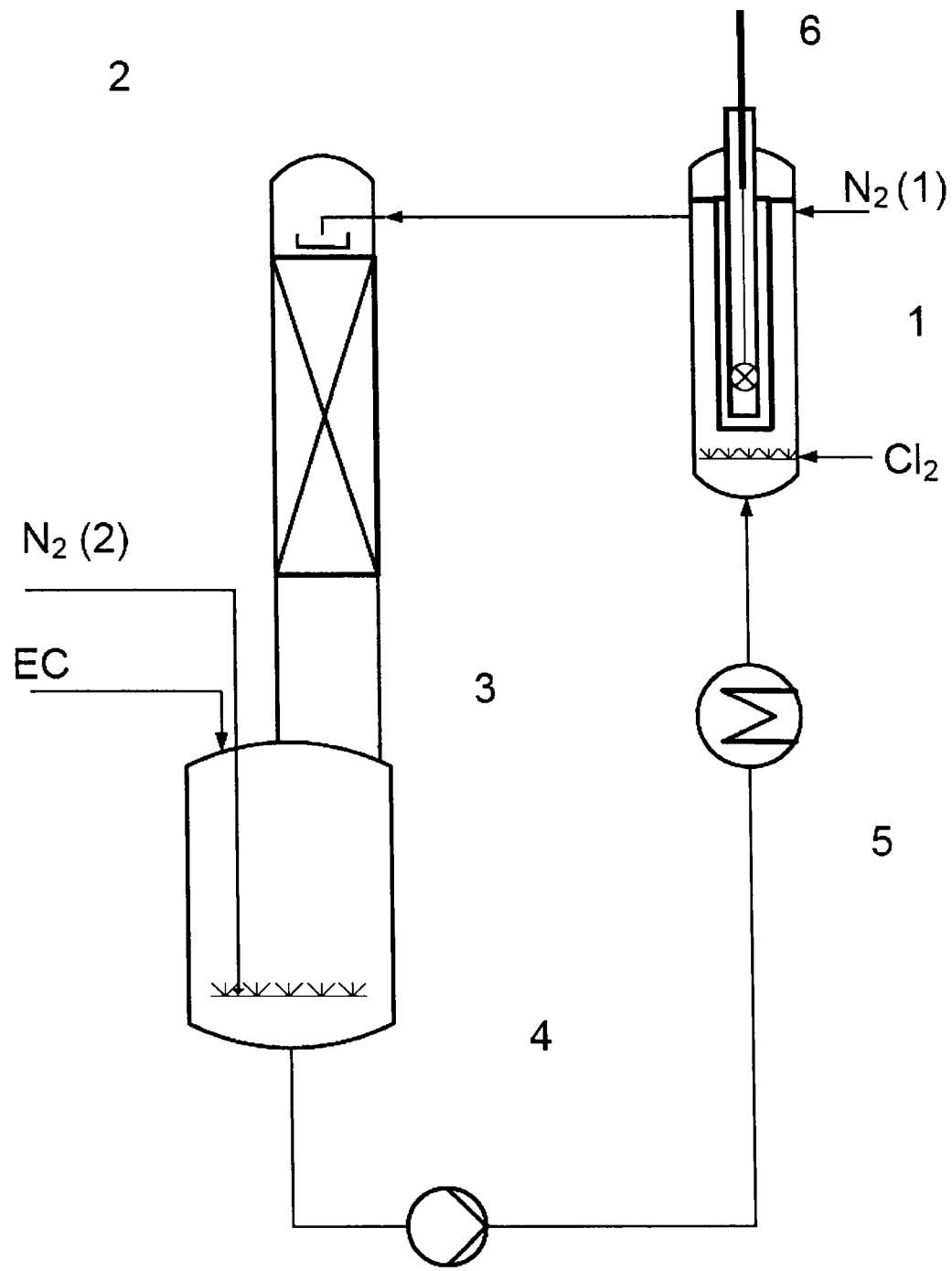
FIG. 1 is a simplified process flow diagram showing an exemplary process for preparing monochloroethylene carbonate according to the present invention.

The reaction of ethylene carbonate (EC) with chlorine gas under the irradiation of UV light ("photochlorination") to form monochloroethylene carbonate (MCEC) is a radical substitution reaction and is depicted in Scheme 1 below.

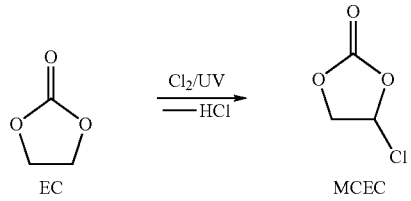

The conversion of monochloroethylene carbonate to vinylene carbonate (VC) by (ii) elimination of hydrogen chloride in depicted in Scheme 2 below.

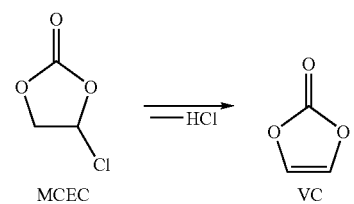

Step (a) of the present process comprises the reaction of ethylene carbonate with chlorine gas in the liquid phase under the irradiation of UV light. Step (b) comprises the introduction of a separate feed of an inert gas into the liquid phase.

Preferably, steps (a) and (b) are performed subsequently, i.e., step (b) is performed after step (a).

At the start of the reaction molten ethylene carbonate typically constitutes the major part of the liquid phase, optionally in combination with a suitable solvent as diluent. Although the liquid phase of the process may be diluted with a suitable solvent it is preferred to conduct the process without adding any solvents. Examples of suitable solvents include chlorinated hydrocarbon solvents such as tetrachloromethane, dichloromethane, chloroform, and tetrachloroethane.

In the course of the reaction monochloroethylene carbonate, cis- and trans-dichloroethylene carbonate, and minor amounts of trichloroethylene carbonate and tetrachloroethylene carbonate form and are thus contained in the liquid phase in addition to non-reacted ethylene carbonate.

In step (a) chlorine gas is introduced into the liquid phase under the irradiation of UV light. The source of UV irradiation is not critical for the present invention and may be any UV irradiation source that is known to the person skilled in the art, such as a UV high-pressure mercury lamp. If desired the UV radiation source may be cooled by appropriate means such as an inert cooling gas or cooling water.

In one embodiment the liquid phase is conveyed, typically let flow by gravity and/or pumped, at least after step (a), and the inert gas that is introduced in step (b) performed after step (a) is passed through the liquid phase countercurrently. Preferably, the liquid phase which is flowed through countercurrently by the inert gas is passed through a means for increasing the contact surface between the liquid phase and the inert gas (in the following "means for increasing the contact surface"). Examples of said means include packed columns such as columns filled with random packings and columns filled with structured packings; tray columns; and spraying the liquid phase into the gaseous phase.

In a preferred embodiment the liquid phase is conveyed, preferably pumped, during both steps (a) and (b) of the present process. More preferably, the liquid phase is circulated while both the chlorine gas and the inert gas are typically introduced continuously. In order to allow circulation of the liquid phase the photochlorination of the ethylene carbonate in step (a) may be performed, for example, in a loop reactor. In an especially preferred embodiment of the present invention the liquid phase is circulated through a loop reactor and the means for increasing the contact surface between the liquid phase and the inert gas. The feed of the inert gas may be introduced into the liquid phase near the outlet of the liquid phase out of the means for increasing the contact surface, typically at its bottom, or at a site located downstream of the means for increasing the contact surface, e.g., into a vessel for receiving the ethylene carbonate starting material.

The photochlorination step (a) may be performed in any type of irradiation reactors resistant to the reaction components involved, especially the chlorine and hydrogen chloride, as they are known to the person skilled in the art. As described above the irradiation reactor may be designed as a loop reactor; in this case the chlorine gas is preferably introduced near the inlet of the liquid phase.

Optionally, an additional feed of an inert gas may be introduced into the liquid phase after step (a) and before step (b). If the liquid phase is circulated through a loop reactor the additional feed of inert gas is preferably added to the irradiation reactor near the outlet of the liquid phase, more preferably it is introduced downstream into an area of the irradiation reactor outside of the reaction zone (irradiation zone).

Typically, during step (a) the temperature of the liquid phase is maintained within a range of from 20 to 70° C., preferably 30 to 50° C. Although lower temperatures generally lead to the formation of less decomposition products the melting point of ethylene carbonate typically requires starting temperatures within the range of from 45 to 50° C. if pure ethylene carbonate is used as starting material. Any increase or decrease of temperature may be achieved by conventional heating or cooling means, respectively.

The type of inert gas employed is not critical for the present invention. Any inert gas that does not react with the starting materials or products can be used. Preferred examples include noble gases such as helium, neon and argon; carbon dioxide; nitrogen and mixtures thereof. It is understood that if the inert gas is fed to the process in more than one feed, the individual feeds need not necessarily comprise the same type of inert gas.

Steps (a) and (b) are preferably conducted at atmospheric pressure.

The conversion of ethylene carbonate can be controlled via the reaction time. The reaction can be stopped when the desired conversion is achieved. The optimum conversion is in the range of from 80 to 85% of ethylene carbonate. If the reaction is performed at higher conversion only the amounts of dichloroethylene carbonate, trichloroethylene carbonate and tetrachloroethylene carbonate increase.

A solvent-free liquid phase obtained by the present process at an ethylene carbonate conversion of from 80 to 85% typically contains, in addition to non-reacted ethylene carbonate, 73 to 85% of monochloroethylene carbonate, 0 to 5% of dichloroethylene carbonate (sum of cis- and trans-isomers), 0 to 1% of trichloroethylene carbonate, 0 to 0.5% of tetrachloroethylene carbonate and 0 to 0.5% of unwanted chlorinated decomposition products as defined above. The amounts are determined by gas chromatography using a flame ionization detector (FID) and the percentages are area % in the gas chromatogram and based on the sum of components of the liquid phase including non-reacted ethylene carbonate.

If desired, exemplary processes according to the present invention may further comprise step (c) isolating the monochloroethylene carbonate. The isolation may be performed by conventional separation techniques, e.g. distillation.

The present inventors have found out that the introduction of an inert gas in the form of a separate feed(s) into the liquid phase considerably lowers the amount of unwanted chlorinated decomposition products of ethylene carbonate. The contact of the liquid phase with the inert gas causes a desorption of hydrogen chloride from the liquid phase. Thus, less decomposition products originating from unwanted reactions of the hydrogen chloride with ethylene carbonate are formed. The unwanted chlorinated decomposition products do not include dichloroethylene carbonate, trichloroethylene carbonate and tetrachloroethylene carbonate. Although monochloroethylene carbonate is the desired end product the di-, tri- and tetrachlorinated ethylene carbonates do not interfere with the subsequent conversion to vinylene carbonate and its purification, and said chlorinated by-products and their possible decomposition products can be separated from the vinylene carbonate easily. The unwanted chlorinated decomposition products include various non-identified chlorinated, probably highly chlorinated organic compounds resulting in unspecific peaks in a gas chromatogram taken from the product mixture. Said unwanted chlorinated decomposition products stay in the vinylene carbonate raw product obtained from monochloroethylene carbonate and are difficult to remove. One way of separating said impurities is the recrystallization of the vinylene carbonate in a mixture of t butyl methyl ether and hexane. Said recrystallization is expensive and can be omitted if monochloroethylene carbonate that is prepared according to exemplary processes of the present invention is used as a starting material for the production of vinylene carbonate.

The liquid phase obtained by the present process for preparing monochloroethylene carbonate may be directly used in a further process converting the monochloroethylene carbonate to vinylene carbonate without any immediate purification steps. It is understood that isolated and purified monochloroethylene carbonate may also be used as a starting material for the conversion to vinylene carbonate; however, for economical reasons, it is preferred to omit any measures to isolate and purify the monochloroethylene carbonate to be used as the starting material.

Ethylene carbonate is converted to vinylene carbonate by eliminating hydrogen chloride, typically by means of a base, preferably a tertiary amine such as triethylamine. The elimination reaction is typically effected in a suitable organic solvent, preferably an ether such as t-butyl methyl ether, diethyl ether, and tetrahydrofuran. In a preferred embodiment the elimination reaction is effected in a mixture of triethylamine and t butyl methyl ether.

In case the liquid phase obtained by the present process for preparing monochloroethylene carbonate is directly used in the elimination reaction without purification it is preferred to determine the amounts of monochloroethylene carbonate and dichloroethylene carbonate in the liquid phase. In the subsequent elimination reaction 1 mole of monochloroethylene carbonate consumes 1 mole of tertiary amine, and 1 mole of dichloroethylene carbonate consumes 2 moles of tertiary amine, the products of the latter reaction have not been identified. Preferably a slight excess, typically about 5%, of tertiary amine is used.

The elimination reaction (ii) is preferably conducted at a temperature within the range of from 30 to 90° C., more preferably from 50 to 70° C. and most preferably from 50 to 68° C. In a preferred embodiment the elimination reaction (ii) is conducted in refluxing t-butyl methyl ether, i.e., at a temperature of about 55° C.

It is preferred to conduct the elimination reaction (ii) at atmospheric pressure, although superatmospheric pressures may also be employed.

The vinylene carbonate raw product may be recovered and purified as it is known in the art. However, it is a major advantage of the present invention that the inconvenient recrystallization step of the vinylene carbonate which was necessary hitherto when product mixtures obtained by the standard process for preparing monochloroethylene carbonate were used may now be omitted. Thus, the vinylene carbonate is preferably purified by thermal separation techniques exclusively. Examples of thermal separation techniques include various conventional continuous distillation and evaporation techniques, such as the use of falling film evaporators, thin film evaporators, and various kinds of columns. It is within the normal skill of the person skilled in the art to select the appropriate separation technique(s) and to adjust the corresponding separation conditions.

Typical yields of isolated vinylene carbonate are within the range of from 50 to 80%, specifically 60 to 70%, based on the amount of monochloroethylene carbonate employed in the elimination step (ii).

The amount of total chlorine (including chloride and organically bound chlorine) in the vinylene carbonate product that has been prepared according to exemplary processes of the present invention and been purified by thermal separation techniques exclusively is typically less than 200 ppm by weight, preferably less than 100 ppm by weight, even more preferably less than 80 ppm by weight and most preferably less than 60 ppm by weight. The amount of total chlorine in a vinylene carbonate product that has been prepared by a previous process, i.e., a process not comprising the introduction of an inert gas as specified by exemplary embodiments of the present invention, and purified by thermal separation techniques exclusively is generally much higher such as about 4500 ppm by weight. The amount of total chlorine is determined by the Wickbold combustion method and ion chromatography.

The purity of the vinylene carbonate product obtained by the present process and purified by thermal separation techniques exclusively is typically at least 99%, preferably at least 99.5% and more preferably at least 99.9%, determined as area % in the gas chromatogram (flame ionization detection).

FIG. 1 is a simplified process flow diagram of a process for preparing monochloroethylene carbonate according to one embodiment of the present invention.

The embodiment of the present invention illustrated in FIG. 1 is a process for preparing monochloroethylene carbonate wherein the liquid phase is circulated through an irradiation reactor 1, a packed column 2 and a receiving vessel 3 by a pump 4. Ethylene carbonate is charged to the receiving vessel 3 before the circulation of the liquid phase is started. Chlorine gas is continuously fed to the liquid phase at the bottom of irradiation reactor 1 which comprises a UV lamp 6. Nitrogen is continuously introduced into the liquid phase in two streams. The first stream of nitrogen $N_2(1)$ is fed at the top area of the irradiation reactor 1 but not into the irradiation zone. The main stream of nitrogen $N_2(2)$ is introduced into the liquid phase at the bottom of the receiving vessel 3. From here it is streaming upwards to and through the packed column 2 where it is countercurrently contacting the liquid phase which is flowing downward. Heat exchanger 5 is used to control the temperature of the liquid phase. Irradiation reactor 1 may comprise cooling means (not shown) such as a cooling jacket flowed through by cooling water.

The following example illustrates the present invention and is not construed to limit it in any way.

Preparation of Monochloroethylene Carbonate

The monochloroethylene carbonate was prepared in a reaction set-up as depicted in FIG. 1. Ethylene carbonate (6.42 kg; 72.95 mol) was first placed in an 8 liter receiving vessel, heated until it melted and then pumped to circulate through the receiving vessel, an irradiation reactor (equipped with a 150 W UV high-pressure mercury lamp Heraeus TQ150) and a 50 mm column filled with random damped glass rings (4 mm in diameter; 4 mm in height) in a height of about 40 cm. The reaction temperature of the liquid phase within the irradiation reactor was maintained in a range of from 45 to 40° C. Chlorine gas was continuously fed at the bottom of the irradiation reactor with a flow rate of about 200 l/h. A first stream of dry nitrogen was continuously fed to the liquid phase at the top area of the irradiation reactor outside the irradiation zone with a flow rate of about 800 l/h. A second stream of dry nitrogen was continuously introduced into the liquid phase at the bottom of the receiving vessel with a flow rate of about 800 l/h. All flow rates of gaseous components were based on volumes standardized to 20° C. and $1.013 \times 10^5$ Pa. The liquid phase was pumped to circulate with a flow rate in the range of from 2 to 3 l/min. After 4.6 kg of chlorine gas had been introduced the reaction was stopped and the liquid phase was analyzed by gas chromatography using a flame ionization detector. The liquid phase contained 80.7% of monochloroethylene carbonate, 15.7% of ethylene carbonate, and 3.5% of dichloroethylene carbonate (sum of cis- and trans-isomers), determined as area % in the gas chromatogram.

Conversion to Vinylene Carbonate kg of diatomaceous earth type filter aid Hyflo Super Cell® were suspended in 115 l of t butyl methyl ether and 64 l (466 mol) of triethylamine were added. The mixture was heated in a stirred tank reactor equipped with a reflux condenser. When the solvent started refluxing 59.3 kg of a monochloroethylene carbonate containing mixture prepared as described above were added into the reactor within 45 min. The mixture was refluxed for 18 h. Then it was cooled to room temperature and the triethylamine was filtered off in form of triethylamine hydrochloride salt formed during the reaction. The filter cake was washed several times with a total of additional 80 l of t butyl methyl ether. The filtrate and the washing liquids were combined and contained about 15% of vinylene carbonate (determined by gas chromatography).

In the above detailed description, reference was made by way of non-limiting examples to preferred embodiments of the invention. Obviously, numerous modifications and variations of the present invention are possible in light of the above teachings. It is therefore to be understood that within the scope of the appended claims, the invention may be practiced otherwise than as specifically described herein.

The invention claimed is:

1. A process for preparing monochloroethylene carbonate, comprising:
   reacting ethylene carbonate with chlorine gas in a liquid phase under irradiation of UV light; and
   introducing a separate feed of an inert gas into the liquid phase;
   wherein introducing the separate feed of the inert gas is performed after reacting ethylene carbonate with chlorine gas.

2. The process according to claim 1, wherein:
   the liquid phase is conveyed at least after reacting ethylene carbonate with chlorine gas; and
   the separate feed of the inert gas is passed through the liquid phase counter currently.

3. The process according to claim 2, wherein the liquid phase is conveyed through a means for increasing a contact surface between the liquid phase and the inert gas.

4. The process according to claim 3, wherein the means for increasing the contact surface between the liquid phase and the inert gas is a packed column.

5. The process according claim 1, wherein the liquid phase is conveyed while reacting ethylene carbonate with chlorine gas and while introducing the separate feed of the inert gas.

6. The process according to claim 5, wherein the liquid phase is conveyed by pumping.

7. The process according to claim 5, wherein the liquid phase is circulated.

8. The process according to claim 1, wherein an additional feed of an inert gas is introduced into the liquid phase after reacting ethylene carbonate with chlorine gas and before introducing the separate feed of the inert gas.

9. The process according to claim 1, wherein a temperature of the liquid phase is maintained within a range of from 20 to 70° C. while reacting ethylene carbonate with chlorine gas.

10. The process according to claim 1, wherein a temperature of the liquid phase is maintained within a range of from 30 to 50° C. while reacting ethylene carbonate with chlorine gas.

11. The process according claim 1, wherein the inert gas comprises at least one member selected from the group consisting noble gases, carbon dioxide and nitrogen.

12. The process according to claim 1, wherein, after reacting ethylene carbonate with chlorine gas and introducing the separate feed of the inert gas, the liquid phase comprises monochloroethylene carbonate, dichloroethylene carbonate, trichloroethylene carbonate, tetrachlororethylene carbonate, and non-reacted ethylene carbonate.

13. The process according to claim 1, wherein the liquid phase is diluted with a suitable solvent.

14. The process according claim 1, further comprising isolating the monochloroethylene carbonate.

15. A process for preparing vinylene carbonate, comprising:
   preparing monochloroethylene carbonate by the process of claim 1; and
   subjecting the monochloroethylene carbonate to an elimination reaction wherein hydrogen chloride is abstracted from the monochloroethylene carbonate to form vinylene carbonate.

16. The process of claim 15, wherein the elimination reaction is effected by a tertiary amine.

17. The process of claim 16, wherein the elimination reaction is effected in a mixture comprising triethylamine and t-butyl methyl ether.

18. The process of claim 15, further comprising recovering and purifying the monochloroethylene carbonate exclusively by thermal separation techniques.

* * * * *